(12) United States Patent
Nigam

(10) Patent No.: US 6,849,090 B2
(45) Date of Patent: Feb. 1, 2005

(54) MYOPIC CORNEAL RING WITH CENTRAL ACCOMMODATING PORTION

(76) Inventor: Alok Nigam, 21381 Birdhollow Dr., Trabuco Canyon, CA (US) 92679

( * ) Notice: Subject to any disclaimer, the term of this patent is extended or adjusted under 35 U.S.C. 154(b) by 0 days.

(21) Appl. No.: 10/610,000

(22) Filed: Jun. 30, 2003

(65) Prior Publication Data

US 2004/0049267 A1 Mar. 11, 2004

Related U.S. Application Data

(63) Continuation of application No. 10/053,178, filed on Nov. 7, 2001, now Pat. No. 6,623,522.

(51) Int. Cl.$^7$ .................................................. A61F 2/14
(52) U.S. Cl. ..................................... 623/5.13; 623/5.16
(58) Field of Search ............................. 623/5.11–5.16, 623/6.14, 4.1

(56) References Cited

U.S. PATENT DOCUMENTS

| | | |
|---|---|---|
| 5,318,047 A | 6/1994 | Davenport et al. |
| 5,391,201 A | 2/1995 | Barrett et al. |
| 5,405,384 A | 4/1995 | Silvestrini |
| 5,805,260 A | 9/1998 | Roffman et al. |
| 5,876,439 A | 3/1999 | Lee |
| 5,888,243 A | 3/1999 | Silverstrini |
| 6,214,044 B1 | 4/2001 | Silverstrini |
| 6,283,595 B1 | 9/2001 | Breger |
| 6,361,560 B1 | 3/2002 | Nigam |
| 6,436,092 B1 * | 8/2002 | Peyman .......................... 606/5 |
| 6,623,522 B2 * | 9/2003 | Nigam ....................... 623/5.13 |

* cited by examiner

*Primary Examiner*—Corrine McDermott
*Assistant Examiner*—Hieu Phan
(74) *Attorney, Agent, or Firm*—Fulbright & Jaworski L.L.P.

(57) ABSTRACT

A bio-compatible corneal ring for myopic correction and accommodation for presbyopia. The corneal ring is made from a bio-compatible material with a lens body having an inner and outer circular edge. The inner circular edge forms an opening in the lens body. The posterior surface of the lens body has a uniform radii of curvature between the inner and outer circular edges. The anterior surface has two radii of curvatures providing for correction of myopia. The first radii of curvature extends from near the outer circular edge to a junction point before the inner circular edge. The second radii of curvature extends from the junction point and continues to the inner circular edge. The inner and outer circular edges have a thickness of less than about 0.020 mm, but preferably are about 0.010 mm or less.

21 Claims, 4 Drawing Sheets

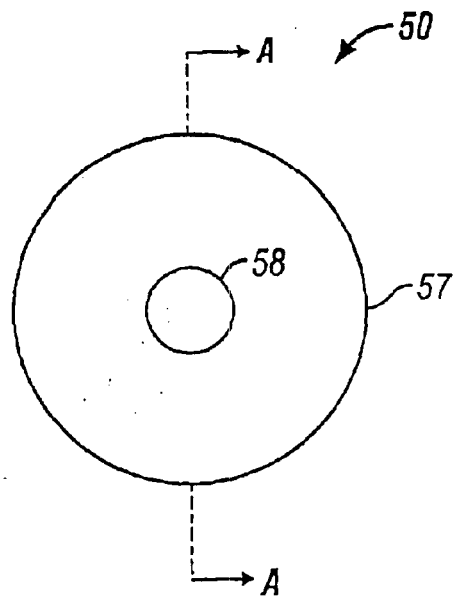
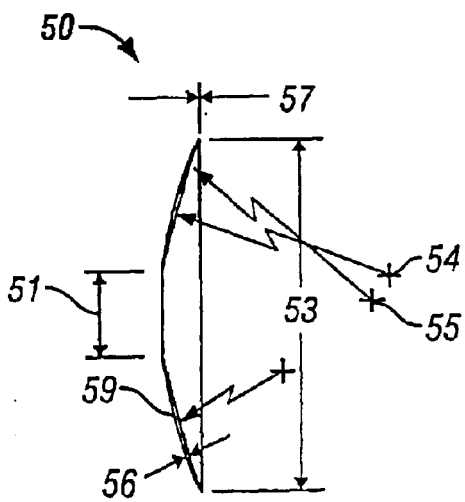
FIG. 8A
FIG. 8B
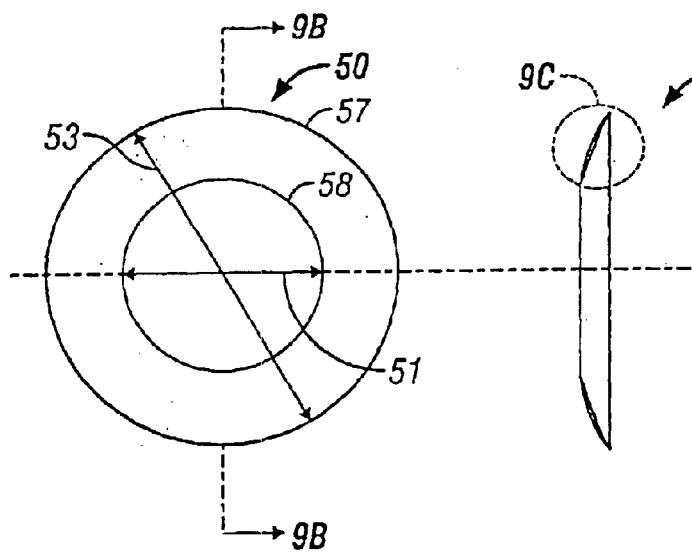
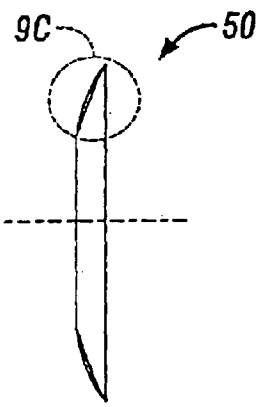
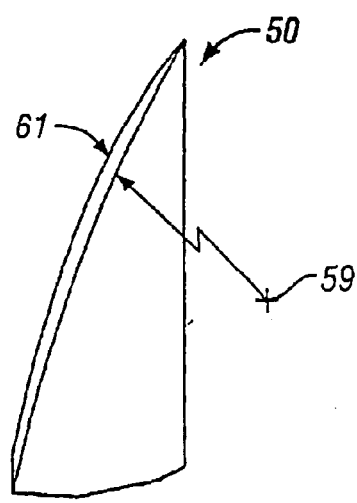
FIG. 9A
FIG. 9B
FIG. 9C

MYOPIC CORNEAL RING WITH CENTRAL ACCOMMODATING PORTION

This application is a continuation of U.S. Ser. No. 10/053,178 filed Nov. 7, 2001, now U.S. PAT. No. 6,623,522, and claims priority thereto.

FIELD OF THE INVENTION

The field of this invention relates to prosthetic implants designed to be implanted in the cornea for modifying the cornea curvature and altering the corneal refractive power for correcting myopia and accommodating for presbyopia.

BACKGROUND OF THE INVENTION

It is well known that anomalies in the shape of the eye can be the cause of visual disorders. Normal vision occurs when light passes through and is refracted by the cornea, the lens, and other portions of the eye, and converges at or near the retina.

In a myopic or near-sighted eye, the cornea is too steeply curved for the length of the eye. This curvature causes light rays to converge at a point before it reaches the retina. Distant objects, therefore, appear out-of-focus or blurry since the light rays are not in focus by the time they reach the retina. Approximately one in four persons have myopic vision.

In persons who are older, a condition called presbyopia occurs in which there is a diminished power of accommodation of the natural lens resulting from the loss of elasticity of the lens. Ordinarily the eye may vary its optical power by focusing the natural lens. However, with the loss of lens elasticity, the eye muscles cannot bend or focus the lens needed for clear vision of near objects. Typically presbyopia begins about the age of 40 and becomes significant after the age of 45.

Corrections for myopia and presbyopia have been attempted primarily through the use of prescriptive lenses in the form of glasses. Many adults wear bifocals or trifocals to correct their vision to see clearly at different distances. Generally, a bifocal lens is arranged such that the upper portion of the lens is used for distance vision and the lower portion for near vision. For reading, a person looks through the lower portion of the lens.

Additionally, available for the correction of myopia and presbyopia are hard, gas-permeable, and soft contact lenses. These contact lenses come in a variety of designs and provide bifocal correction. Also known for multi-vision correction are diffractive contact lenses where the surface of the lenses have invisible ridges molded into concentric circles. Generally, light passing through the lens is bent so that the wearer's near and distant vision is corrected. Few persons of older age, however, are able to adjust to the use of contact lenses. This is especially true as many older persons have trouble inserting and removing the contacts on a daily basis from their eyes.

Also, correction of myopia through the use of various corneal implants within the body of the cornea have been suggested. Various designs for such implants include solid and split-ring shaped, circular flexible body members and other types of ring-shaped devices that are adjustable. These implants are inserted within the body of the cornea for changing the shape of the cornea, thereby altering the its refractive power. Although these corneal implants attempt to correct for the myopic condition, they do not adequately accommodate for presbyopia.

BRIEF SUMMARY OF THE INVENTION

The present invention is directed to a bio-compatible corneal implant for correction of myopia and accommodation for presbyopia. The corneal implant is ring-shaped and made from a bio-compatible material with a lens body having an inner and outer circular edge. The inner circular edge forms an opening in the lens body. The posterior surface of the lens body has a uniform radii of curvature between the inner and outer circular edges. The anterior surface has two radii of curvatures. The first radii of curvature extends from near the outer circular edge to a junction point before the inner circular edge. The second radii of curvature extends from the junction point and continues to the inner circular edge. In one embodiment, an aspherical surface transitions the first radii to the second radii of curvature. This aspherical curvature provides a smooth transition between each radii of curvature which reduces the thickness of the junction point. The inner and outer circular edges have a thickness less than about 0.020 mm and preferably about 0.010 mm.

The corneal implant, when placed under a lamellar dissection made in the cornea (such as a corneal flap), to relieve tension of Bowman's membrane, alters the outer surface of the cornea to correct the refractive error of the eye. By relieving the pressure and subsequent implantation of the device, the pressure points which typically are generated in present corneal surgeries are eliminated, and hence reduces risk to patients of extrusion of implants. Unlike an implant placed in an intact cornea where corneal tissue can be deflected anteriorly or posteriorly leading to unpredictable refractive correction, proper relief of the pressure due to dissection of the Bowman's membrane ensures that all the corneal changes take place at the anterior surface.

For the correction of myopia, the implant is shaped into a meniscus lens with an anterior surface of the second radii of curvature being flatter than the posterior surface. When the implant is placed concentrically on the stromal bed the curvature of the anterior surface of the cornea in the optic zone is flattened to the extent appropriate to achieve the desired refractive correction.

For the accommodation of presbyopia, the corneal implant has a circular hole. When implanted on the stromal bed and the corneal flap is positioned over the anterior surface of the corneal implant, a slight anterior oriented curvature is thereby retained in the center of the cornea leaving extra power needed for near vision, thus correcting for presbyopia.

The material from which the corneal implants are made is preferably a clear, permeably, microporous hydrogel with a water content greater than 40% up to approximately 90%. The refractive index should be substantially identical to the refractive index of corneal tissue. Other bio-compatible materials from which the corneal implant may be made, include: polymethlmethacrylate (PMMA), silicone polymers, UV-absorbing acrylic, hydrogel, micro-porous hydrogel, collamer, collagel acrylic polymers, and other composite materials.

The refractive index of the implant material should be in the range of 1.36–1.39, which is substantially similar to that of the cornea (1.376). This substantially similar refractive index prevents optical aberrations due to edge effects at the cornea-implant interface.

BRIEF DESCRIPTION OF THE DRAWINGS

A better understanding of the invention can be obtained from the detailed description of exemplary embodiments set forth below, when considered in conjunction with the appended drawings, in which:

FIG. 8a is a schematic illustrating a top view of the corneal implant;

FIG. 8b is a schematic illustrating a cross-section of the corneal implant shown in FIG. 8a;

FIG. 9a is a schematic illustrating a top view of the corneal implant;

FIG. 9b is a schematic illustrating a cross-section of the corneal implant shown in FIG. 9a illustrating an aspherical blended surface;

FIG. 9c is a blown-up view of part of FIG. 9b illustrating an aspherical blended surface;

DETAILED DESCRIPTION OF THE INVENTION

Figure 1:
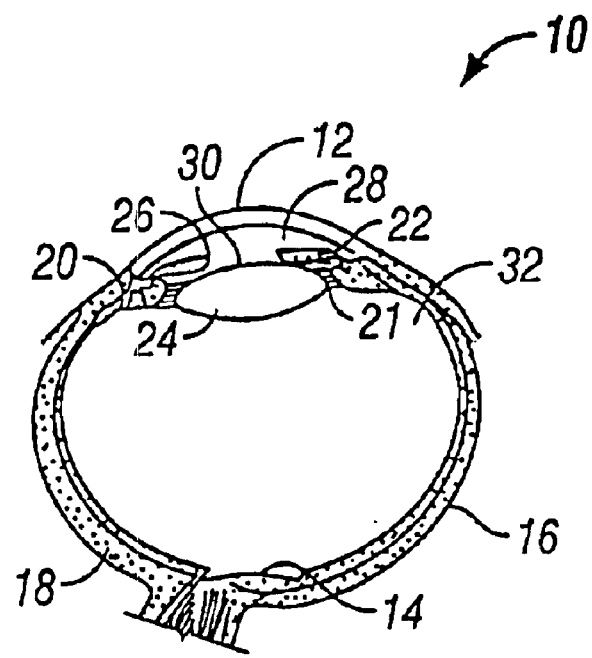
FIG. 1 is a schematic illustration of a horizontal section of a human eye.

Referring first to FIG. 1 of the drawings, a schematic representation of the globe of the eye 10 is shown, which resembles a sphere with an anterior bulged spherical portion 12 that represents the cornea. The eye 10 is made up of three concentric coverings that enclose the various transparent media through which light must pass before reaching the light sensitive retina 14.

The outer-most covering is a fibrous protective portion that includes a posterior layer which is white and opaque, called the sclera 16, which is sometimes referred to as the white of the eye where it is visible from the front. The anterior ⅙th of this outer layer is the transparent cornea 12.

A middle covering is mainly vascular and nutritive in function and is made up of the choroid 18, the ciliary 20 and the iris 22. The choroid generally functions to maintain the retina. The ciliary muscle 21 is involved in suspending the lens 24 and accommodating the lens. The iris 22 is the most anterior portion of the middle covering of the eye and is arranged in a frontal plane. The iris is a thin circular disc corresponding to the diaphragm of a camera, and is perforated near its center by a circular aperture called the pupil 26. The size of the pupil varies to regulate the amount of light that reaches the retina 14. It contracts also to accommodate, which serves to sharpen the focus by diminishing spherical aberrations. The iris 22 divides the space between the cornea 12 and the lens 24 into an anterior chamber 28 and posterior chamber 30.

The inner-most covering is the retina 14, consisting of nerve elements which form the true receptive portion for visual impressions that are transmitted to the brain. The vitreous 32 is a transparent gelatinous mass which fills the posterior ⅘ths the globe 10. The vitreous supports the ciliary body 20 and the retina 14.

In the normal (emmetropic) eye, objects are properly focused on the retina. A number of factors determine how light rays are focused on the retina. Basically, these include the shape of the cornea, the power of the natural lens, and the length of the eye. The shape of the cornea determines a fixed refractive power. If the cornea is too steeply curved relative to the length of the eye or if the eye is too long relative to the curvature of the cornea, then myopia results. If the cornea is too flat or the eye too short, then hyperopia results. In the normal eye, the shape of the natural lens can change thereby causing a change in the refractive power of the natural lens allowing the eye to change its focal point.

Figure 2:
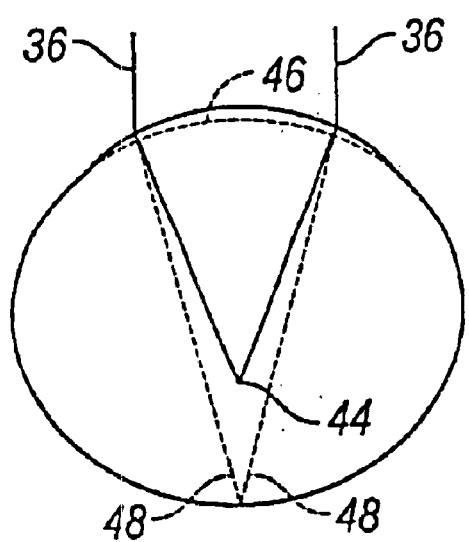
FIG. 2 is a schematic illustration of an eye system showing adjustment of the cornea to flatten the corneal slope to correct for myopia.
Figure 3:
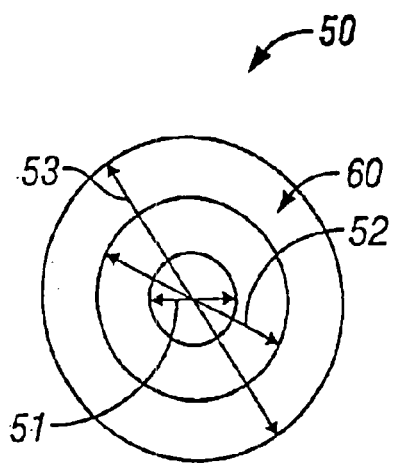
FIG. 3 is a 3-dimensional top view of one embodiment of the corneal implant.
Figure 4:
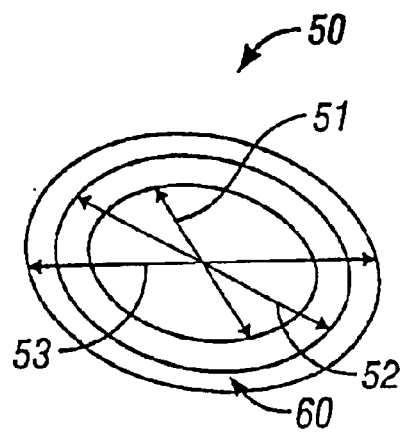
FIG. 4 is a 3-dimensional top view of another embodiment of the corneal implant.
Figure 5:
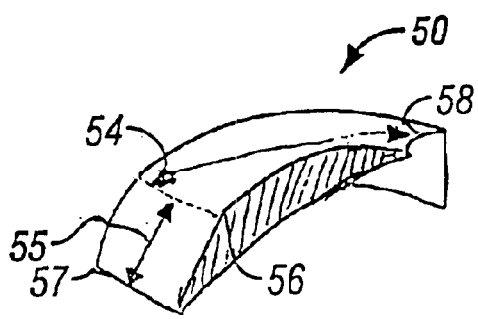
FIG. 5 is a 3-dimensional, cross-sectional top view of the corneal implant.
Figure 6:
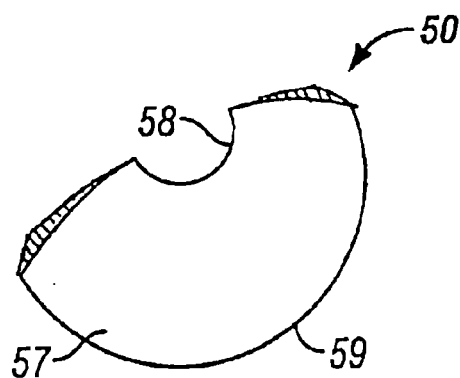
FIG. 6 is a 3-dimensional, cross-sectional bottom view of the corneal implant.
Figure 7:
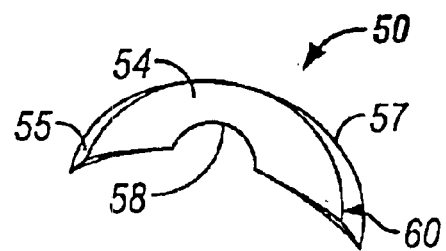
FIG. 7 is a cross-sectional top view of the corneal implant.

Referring to FIG. 2 of the drawings, the globe of an eye 10 is shown as having a cornea 12 with a normal curvature represented by a solid line 34. For people with normal vision, when parallel rays of light 36 pass through the corneal surface 34, they are refracted by the corneal surfaces to converge eventually near the retina 14 (FIG. 1). The diagram of FIG. 2 discounts, for the purposes of this discussion, the refractive effect of the lens or other portions of the eye.

Typical of the myopic eye, the normal corneal curvature causes the light rays 36 to focus at a point 44 in the vitreous which is short of the retinal surface. If the cornea is flattened as shown by dotted lines 46 through the use of a properly-shaped corneal implant, light rays 36 will be refracted at a smaller angle and converge at a more distant point such as directly on the retina 14 as shown by dotted lines 48.

The above common refractive disorders of myopia and presbyopia are measured in units called diopters. Diopters represent the amount of correction needed to normalize vision. Ordinarily a prescription is written in three numbers ±A ±B×C. A identifies the degree of nearsightedness or farsightedness. The plus sign indicates farsightedness and the minus sign indicates nearsightedness. B identifies the degree of astigmatism. C is the axis identifying the degree of astigmatism. The more nearsighted, farsighted, or astigmatic a person is, the higher the prescription will be in diopters.

The refractive correction needed for each individual is specific to the persons shape of the eye and cornea. In selecting the proper dimensions of the corneal implant for a patient the refractive correction for myopia and presbyopia must be determined. Generally, this includes determine the K-value or steepness of the cornea, what myopic correction is needed, and what presbyopic add (power) is needed. These requirements determine the size of the central hole.

FIGS. 3–7 illustrate the inventive corneal implant 50. The corneal implant has an inside diameter 51, an optical zone 52, and an outside diameter 53. The outside diameter and the inside diameter each have an edge thickness, 57 and 58 respectively. The inner and outer circular edges have a thickness of less than about 0.020 mm and preferably are about 0.010 mm.

The anterior surface of the corneal implant has a first radii of curvature 55 and a second radii of curvature 54. The first radii of curvature 55 begins from the outside diameter 53 and continues to a junction point 60 between the inside and outside diameters 51, 53. The second radii of curvature 54 continues from the junction point 60 and extends to the inside diameter 51. The posterior radii of curvature 59 extends from the outside diameter 53 to the inside diameter 51. A junction point 60 exists between the first radii of curvature 55 and the second radii of curvature 54. A junction thickness is defined between the junction point 60 and the posterior radii of curvature.

The inner diameter is preferably between about 2 and 4 mm, although the inner diameter may exceed this range and may be configured in various increments according to the needs of the patient. Variation of the inner diameter allows differing amounts of central power add to be achieved. The central cornea is centrally steeped which provides a central power add at the anterior cornea surface. Generally, the central power add provides presbyopic correction up to about +4 diopters. However, a greater power add correction may be obtained.

FIGS. 8a and 8b further illustrate the inventive corneal implant. FIG. 8a is a schematic illustrating a top view of the corneal implant. FIG. 8b is a schematic illustrating a cross-section of the corneal implant shown in FIG. 8a.

In one embodiment, an aspherical surface transitions the first radii to the second radii of curvature. This aspherical curvature provides a smooth transition between each radii of curvature. FIGS. 9a–9b are schematics illustrating a blended aspherical surface 61 blending the first and second anterior radii of curvature. FIG. 9b is a schematic illustrating a cross-section of the corneal implant shown in FIG. 9a illustrating an aspherical blended surface. FIG. 9c is a blown-up view of part of FIG. 9b illustrating an aspherical blended surface 61.

Table 1 is illustrative of various lens dimensions of the inventive corneal implant 50 showing myopia correction ranging from about −1 to about −12 diopters. Dimensions of the lens may be changed to achieve other myopic and presbyopic correction. Accordingly, the table is not meant to limit the scope of dimensions of the corneal implant. For the table below, the outside diameter 53 is 7.000 mm, the optical zone 52 is 6.000 mm, the inside diameter 51 is 2.000 mm, the inner diameter edge thickness is 0.010 mm, the outer diameter edge thickness is 0.010 mm. In the table each radius and the junction thickness is represented in mm.

TABLE 1

| DIOPTER | JUNCTION THICKNESS | POSTERIOR RADIUS | FIRST RADIUS R1 | SECOND RADIUS R2 |
|---|---|---|---|---|
| −1.00 | 0.013 | 7.000 | 6.855 | 7.135 |
| −2.00 | 0.026 | 7.000 | 6.595 | 7.275 |
| −3.00 | 0.038 | 7.000 | 6.364 | 7.420 |
| −4.00 | 0.051 | 7.000 | 6.157 | 7.571 |
| −5.00 | 0.063 | 7.000 | 5.971 | 7.729 |
| −6.00 | 0.076 | 7.000 | 5.804 | 7.894 |
| −7.00 | 0.088 | 7.000 | 5.652 | 8.065 |
| −8.00 | 0.101 | 7.000 | 5.514 | 8.244 |
| −9.00 | 0.113 | 7.000 | 5.388 | 8.432 |
| −10.00 | 0.126 | 7.000 | 5.272 | 8.628 |
| −11.00 | 0.138 | 7.000 | 5.167 | 8.833 |
| −12.00 | 0.151 | 7.000 | 5.069 | 9.049 |

Table 2 further illustrates various lens dimensions of the inventive corneal implant 50 showing myopia correction ranging from about −1 to about −12 diopters. Dimensions of the lens may be changed to achieve other myopic and presbyopic correction. Accordingly, the table is not meant to limit the scope of dimensions of the corneal implant. For the table below, the outside diameter 53 is 6.000 mm, the optical zone 52 is 5.500 mm, the inside diameter 51 is 4.000 mm, the inner diameter edge thickness is 0.010 mm, the outer diameter edge thickness is 0.010 mm. In the table each radius and the junction thickness is represented in mm.

TABLE 2

| DIOPTER | JUNCTION THICKNESS | POSTERIOR RADIUS | FIRST RADIUS R1 | SECOND RADIUS R2 |
|---|---|---|---|---|
| −1.00 | 0.011 | 6.700 | 6.490 | 6.823 |
| −2.00 | 0.021 | 6.700 | 6.047 | 6.951 |
| −3.00 | 0.032 | 6.700 | 5.683 | 7.084 |
| −4.00 | 0.042 | 6.700 | 5.379 | 7.222 |
| −5.00 | 0.053 | 6.700 | 5.123 | 7.365 |
| −6.00 | 0.063 | 6.700 | 4.905 | 7.514 |
| −7.00 | 0.073 | 6.700 | 4.718 | 7.670 |
| −8.00 | 0.084 | 6.700 | 4.556 | 7.831 |
| −9.00 | 0.094 | 6.700 | 4.415 | 8.000 |
| −10.00 | 0.104 | 6.700 | 4.291 | 8.177 |
| −11.00 | 0.114 | 6.700 | 4.182 | 8.361 |
| −12.00 | 0.125 | 6.700 | 4.085 | 8.554 |

Figure 10A:
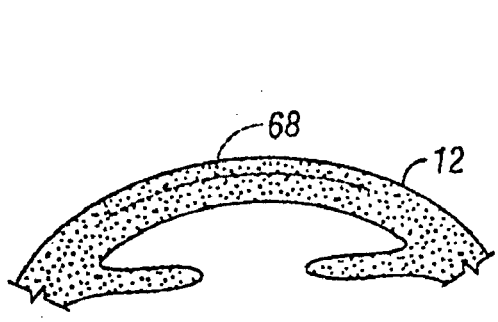
FIGS. 10a and 10b are schematic representations of a lamellar dissectomy, with FIG. 10b showing in particular the portion of the dissected cornea being connected through a hinge to the intact cornea.
Figure 10B:
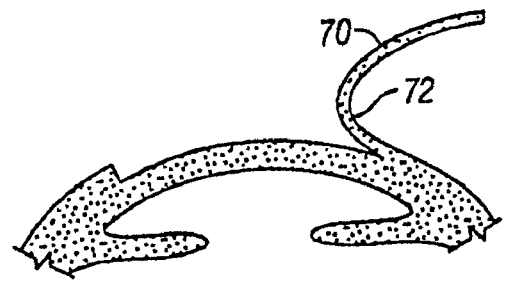

The present corneal implant 50 can be implanted in the cornea using a lamellar dissectomy shown schematically in FIGS. 10a, 10b. In this procedure, a keratome (not shown) is used in a known way to cut a portion of the outer surface of the cornea 12 along dotted lines 68 as shown in FIG. 10a. This type of cut is used to form a corneal flap 70 shown in FIG. 10b, which remains attached to the cornea 12 through what is called a hinge 72. The hinge 72 is useful for allowing the flap 70 to be replaced with the same orientation as before the cut.

Figure 10C:
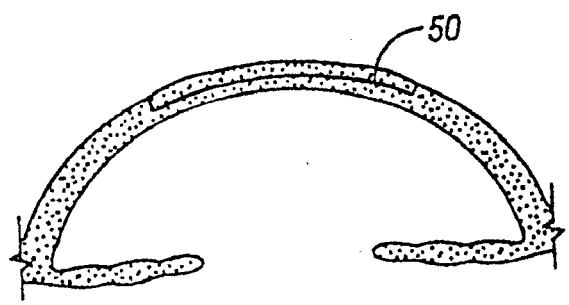
FIG. 10c is a schematic representations of a cornea in which the corneal implant have been implanted lamellar for a myopic correction and accommodation for presbyopia.

As is also known in the art, the flap is cut deeply enough to dissect the Bowman's membrane portion of the cornea, such as in keratome surgery or for subsequent removal of the tissue by laser or surgical removal. A corneal flap of 100 to 200 microns, typically 160 to 200 microns, is made to eliminate the Bowman's membrane tension (which minimizes corneal nerve damage). This helps to conform the flap to the lens surface, thereby transferring all of the change of the shape to the anterior surface of the cornea. This makes refractive correction more reliable and predictable. Also, the possibility of extrusion of the implants is reduced due to pressure generated within the cornea caused by the addition of the implant. The corneal implant 50 is shown implanted in the cornea in FIG. 10c respectively, after the flap has been replaced in its normal position. These figures show the corrected shape for the outer surface of the cornea as a result of implants of the shapes described.

Figure 11:
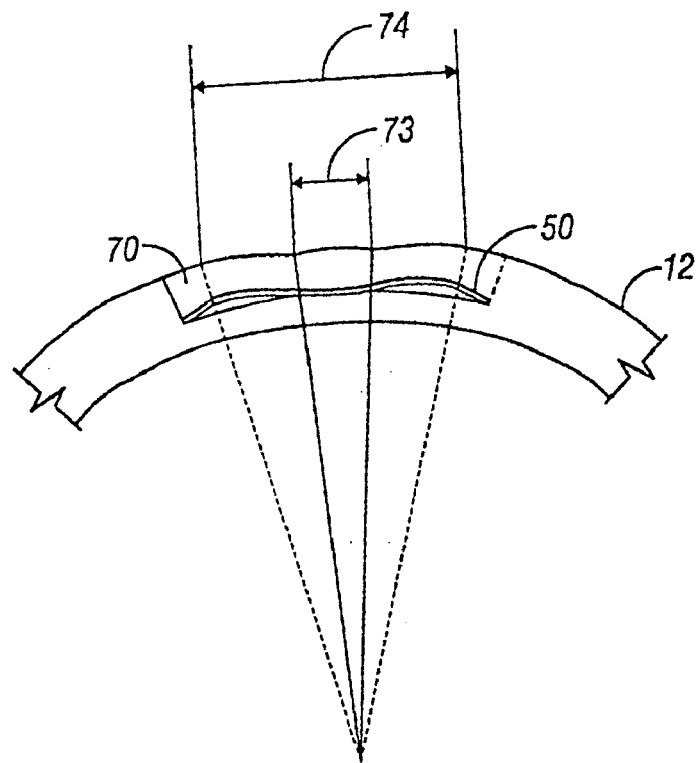
FIG. 11 is a schematic illustrating the use of the corneal implant for correction of myopia and accommodation of presbyopia.

FIG. 11 is a basic schematic illustrating the use of the corneal implant for correction of myopia and accommodation of presbyopia. The lens 50 is shown implanted in the cornea 12. The corneal flap 70 is shown positioned on the anterior surface of the corneal implant 50. When viewing distant objects, light rays 74 entering the cornea pass through the optical zone and inner diameter of the lens 50. Using the correct myopic diopter correction, distant object become clear. The center of the object remains unfocused, but is not descernable by the eye.

When viewing near objects, such as text in a book, the eye utilizes the light rays 73 entering through the center portion of the cornea. As illustrated, the corneal flap 70 as laid over the corneal implant 50 provides for a presbyopic diopter correction. Thus, the wearer of the implant may focus on near objects, as well as distant objects.

Although one or more embodiments of the present invention has been shown or described, alternative embodiments will be apparent to those skilled in the art and are within the intended scope of the present invention.

What is claimed is:

1. A corneal implant for correcting myopia and accommodating for presbyopia, said implant comprising:
   a lens body being made of optically clear bio-compatible material, the lens body having an anterior surface and a posterior surface and having an inner diameter edge and an outer diameter edge, the inner diameter edge forming a central opening in the lens body;
   the posterior surface being curved in shape with a posterior radii of curvature; and
   the anterior surface being curved in shape with a first anterior radii of curvature and a second anterior radii of curvature;
   wherein an aspherical surface transitions the first radii of curvature to the second radii of curvature, and the anterior surface of the second radii of curvature being flatter than the posterior surface radii of curvature.

2. The corneal implant of claim 1, wherein the posterior radii of curvature extends from the outer diameter edge to the inner diameter edge.

3. The corneal implant of claim 1, wherein the first anterior radii of curvature begins adjacent to the outer diameter edge and ends near a junction point, and the second radii of curvature begins from near the junction point and ends near the inner diameter edge.

4. The corneal implant of claim 1, 2 or 3, wherein the first anterior radii of curvature is less than the second anterior radii of curvature.

5. The corneal implant of claim 1, wherein the inner diameter edge thickness is less than about 0.020 mm.

6. The corneal implant of claim 1, wherein the inner diameter edge thickness is about 0.010 mm.

7. The corneal implant of claim 1, wherein the outer diameter edge thickness is less than about 0.020 mm.

8. The corneal implant of claim 1, wherein the outer diameter edge thickness is about 0.010 mm.

9. The corneal implant of claim 1, wherein the inner diameter edge thickness and the outer diameter edge thickness is less than about 0.020 mm.

10. The corneal implant of claim 1, wherein the inner diameter edge thickness and the outer diameter edge thickness is about 0.010 mm.

11. The corneal implant of claim 1, wherein the diameter of the outer diameter edge is between about 5 mm and about 7 mm.

12. The corneal implant of claim 1, wherein the diameter of the inner diameter edge is between about 2 mm and about 4 mm.

13. The corneal implant of claim 1, wherein the diameter of the outer diameter edge is between about 5 mm and about 7 mm and the diameter of the inner diameter edge is between about 2 mm and about 4 mm.

14. The corneal implant of claim 1, wherein the clear bio-compatible material consists essentially of any one of the group of hydrogel, microporous hydrogel, polymethyl methacrylate, silicone polymers, UV-absorbing acrylic, acrylic polymers, collamer, and collagel.

15. The corneal implant of claim 1, wherein the corneal implant is adapted for myopic diopter correction ranging from about −1 to about −12 diopters.

16. The corneal implant of claim 1, wherein the corneal implant is adapted for presbyopic diopter correction ranging to about +4 diopters.

17. The corneal implant of any of claims 1, wherein the bio-compatible material has a refractive index substantially identical to the refractive index of corneal tissue.

18. A corneal implant for correcting myopia and accommodating for presbyopia, said implant comprising:
   a lens body being wade of optically clear bio-compatible material, the lens body having an anterior surface and a posterior surface and having an inner diameter edge and an outer diameter edge, the inner diameter edge forming a central opening in the lens body;
   the posterior surface being curved in shape with a posterior radii of curvature, the posterior surface extending from the outer diameter edge to the inner diameter edge; and
   the anterior surface being curved in shape with a first anterior radii of curvature and a second radii of curvature;
   wherein a continuous aspheric surface transitions the first anterior radii of curvature with the second anterior radii of curvature;
   wherein the inner diameter edge thickness and the outer diameter edge thickness are less than about 0.020 mm;
   wherein the anterior surface of the second radii of curvature being flatter than the posterior surface radii of curvature;
   wherein the bio-compatible material has a refractive index substantially identical to the refractive index of corneal tissue; and
   wherein the clear bio-compatible material consists essentially of any one of the group of hydrogel, microporous hydrogel, polymethyl methacrylate, silicone polymers, UV-absorbing acrylic, acrylic polymers, collamer, and collagel.

19. The corneal implant of claim 18, wherein the diameter of the outer diameter edge is between about 5 mm and about 7 mm and the diameter of the inner diameter edge is between about 2 mm and 4 mm.

20. The corneal implant of claim 18, wherein the corneal implant is adapted for myopic diopter correction ranging from about −1 to about −12 diopters.

21. The corneal implant of claim 18, wherein the corneal implant is adapted for presbyopic diopter correction ranging to about +4 diopters.

* * * * *